United States Patent [19]

Heindl et al.

[11] Patent Number: 5,183,925
[45] Date of Patent: Feb. 2, 1993

[54] LEUKOTRIENE-B4 DERIVATIVES, PROCESS FOR THEIR PRODUCTION AND THEIR USE AS PHARMACEUTICAL AGENTS

[75] Inventors: Josef Heindl; Werner Skuballa; Bernd Buchmann; Wolfgang Frohlich; Rolalnd Ederdt, all of Berlin, Fed. Rep. of Germany

[73] Assignee: Schering Aktiengesellschaft, Berlin and Bergkamen, Fed. Rep. of Germany

[21] Appl. No.: 623,386

[22] PCT Filed: Mar. 16, 1990

[86] PCT No.: PCT/DE90/00209
§ 371 Date: Nov. 19, 1990
§ 102(e) Date: Nov. 19, 1990

[87] PCT Pub. No.: WO90/11272
PCT Pub. Date: Oct. 4, 1990

[30] Foreign Application Priority Data

Mar. 17, 1989 [DE] Fed. Rep. of Germany ....... 3909326

[51] Int. Cl.$^5$ .............................................. C07C 69/76
[52] U.S. Cl. ...................................... 560/61; 560/62; 560/63; 562/471; 562/472
[58] Field of Search ........................... 560/61; 562/471

[56] References Cited

FOREIGN PATENT DOCUMENTS 0109225 5/1984 European Pat. Off. .

OTHER PUBLICATIONS

CA 57: 15046d, 1962.

Primary Examiner—Paul J. Killos
Attorney, Agent, or Firm—Millen, White, Zelano and Branigan

[57] ABSTRACT

The invention relates to leukotriene-B4 derivatives of formula I,

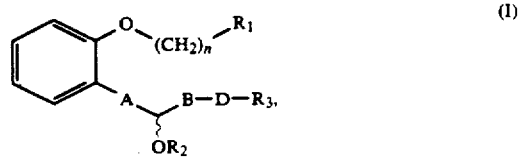

in which
n=1-10,
$R_1$ means radical $CH_2OH$, radical $COOR_4$, radical $CONHR_5$ or radical $CONR_6R_7$,
A means a cis, trans or trans, trans—CH=CH—CH=CH group or tetramethylene group,
B means an alkylene group with up to 10 C atoms,
D means a direct compound, oxygen, sulfur, a —C≡C group or a —CH=CR$_8$ group,
B and D together mean a direct bond,
$R_2$ means a hydrogen atom or an acid radical of an organic acid with 1-15 C atoms and
$R_3$ means a hydrogen atom, an optionally substituted alkyl radical with 1-10 C atoms,
a cycloalkyl radical with 3-10 C atoms, an optionally substituted aryl radical with 6-10 C atoms or a 5-6 member heterocyclic radical and if $R_4$ means a hydrogen atom, their salts with physiologically compatible bases and their cyclodextrin clathrates, process for their production and their pharmaceutical use.

5 Claims, No Drawings

LEUKOTRIENE-B4 DERIVATIVES, PROCESS FOR THEIR PRODUCTION AND THEIR USE AS PHARMACEUTICAL AGENTS

The invention relates to new leukotriene-B4 derivatives, the process for their production as well as their use as a pharmaceutical agents.

Leukotriene-B4 (LTB4) was discovered in 1979 by B. Samuelsson et al. as a metabolite of arachidonic acid. In the biosynthesis, leukotriene A4 is formed by the enzyme 5-lipoxygenase first as a central intermediate product, which then is converted by a specific hydrolase to the LTB4.

effective, i.e., it triggers a directed migration of leukocytes in the direction of a gradient of increasing concentration. Further, because of its chemotactic activity, it indirectly changes the vascular permeability, and a synergism with prostaglandin $E_2$ was observed. LTB4 obviously plays a decisive role in inflammatory, allergic and immunological processes.

Leukotrienes and especially LTB4 are involved in skin diseases, which accompany inflammatory processes (increased vessel permeability and formation of edemas, cell infiltration), increased proliferation of skin cells and itching, such as, for example, in eczemas, erythemas, psoriasis, pruritus and acne. Pathologically increased leukotriene concentrations are involved ei-

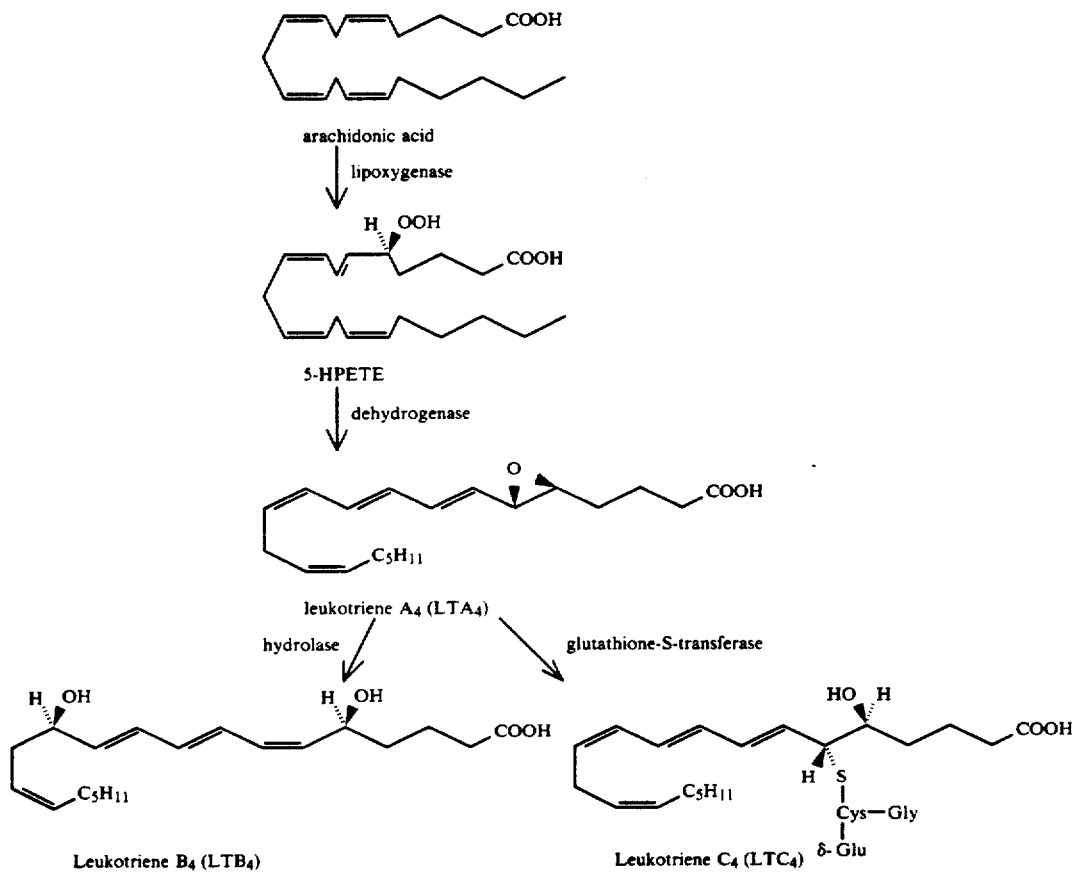

The nomenclature of the leukotrienes can be gathered from the following works:

a) B. Samuelsson et al., Prostaglandins 19, 645 (1980); 17, 785 (1979).

b) C. N. Serhan et al., Prostaglandins 34, 201 (1987).

The physiological and especially the pathophysiological importance of Leukotriene B4 is summarized in several more recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson et al., Science 237, 1171 (1987). d) C. W. Parker, Drug Development Research 10 277 (1987). It follows from the above that LTB4 is an important inflammation mediator for inflammatory diseases, in which leukocytes invade the affected tissue.

It is known that LTB4 causes the adhesion of leukocytes on the blood vessel wall. LTB4 is chemotactically ther causally in the development of many dermatitides or there is a connection between the persistence of the dermatitides and the leukotrienes. Clearly increased leukotriene concentrations were measured, for example, in the skin of patients with psoriasis or atopic dermatitis.

Further, leukotrienes and LTB4 are involved especially in arthritis, chronic lung disease (e.g., asthma), rhinitis and inflammatory intestinal diseases.

Antagonists against LTB4 itself or inhibitors of those enzymes, which are involved in the synthesis of the LTB4, can be effective as specific medications, especially against diseases which accompany inflammations and allergic reactions.

Besides the therapeutic possibilities, which can be derived from an antagonizing of LTB4 with LTB4 analogs, the usefulness and potential use of leukotriene B4 agonists for the treatment of fungus diseases of the skin was also able to be shown recently (H. Kayama, Prostaglandins 34, 797 (1988)).

The replacement of the chemically and metabolically labile cis-delta[6,7] double bond of $LTB_4$ by a 1,2-substituted phenyl ring results in the more stable 6,7-interphenylene-leukotrienes, and antagonists, agonists and partial antagonists are obtained depending on the structural change of the functional groups and depending on the tissue type. It has now been found that by the substitution of the 5-hydroxymethyl group by an oxygen atom and by other derivatizing of the function groups, $LTB_4$ analogs are obtained which greatly antagonize the action of the natural $LTB_4$. Duration of action and selectivity of the new compounds could be further improved by lower oxidation sensitivity or the abscence of a tendency toward lactonization because of the nonexistent 5-hydroxy group.

The invention relates to a new leukotriene-$B_4$ derivatives of formula I,

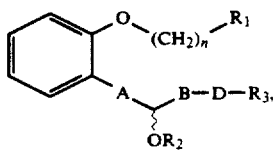

in which n = 1–10, $R_1$ means radical $CH_2OH$, radical $COOR_4$ with $R_4$ meaning a hydrogen atom, an alkyl radical with 1–10 C atoms, a cycloalkyl radical with 3–10 C atoms, an aryl radical with 6–10 C atoms optionally substituted by 1–2 chlorine, bromine, phenyl, alkyl with 1–4 C atoms, chloromethyl, fluoromethyl, trifluoromethyl, carboxy, $C_1$-$C_4$ alkoxy or hydroxy, a —$CH_2$—CO aryl radical with 6–10 C atoms for an aryl or a 5–6-member heterocyclic radical with at least 1 heteroatom, radical $CONHR_5$ with $R_5$ meaning an alkanoyl radical or an alkanesulfonyl radical with 1–10 C atoms or radical $R_4$ or radical $CONR_6R_7$, in which $R_6$ and $R_7$ mean an alkyl with 1–10 C atoms or together, an alkylene radical with 3–6 C atoms, A means a cis, trans or trans, trans—CH= CH—CH=CH— group or a tetramethylene group, B means a straight-chain or branched-chain, saturated or unsaturated alkylene group with up to 10 C atoms which can optionally be substituted by fluorine, or the group

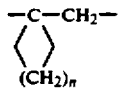

with n = 1, 2 or 3,

D means a direct compound, oxygen, sulfur, a —C≡C group or a —CH=$CR_8$ group with $R_8$ as hydrogen, $C_1$-$C_5$ alkyl, chlorine or bromine, B and D together mean a direct bond, $R_2$ means a hydrogen atom or an acid radical of an organic acid with 1–15 C atoms and $R_3$ means a hydrogen atom, an alkyl radical with 1–10 C atoms, an alkyl radical with 1–10 C atoms substituted by chlorine or bromine, a cycloalkyl radical with 3–10 C atoms, an aryl radical with 6–10 C atoms substituted optionally by 1-2 chlorine, bromine, phenyl, alkyl with 1–4 C atoms, chloromethyl, fluoromethyl, trifluoromethyl, carboxy, $C_1$-$C_4$ alkoxy or hydroxy or a 5–6-member heterocyclic radical with at least 1 heteroatom and, if $R_5$ means a hydrogen atom, their salts with physiologically compatible bases and their cyclodextrin clathrates.

As alkyl groups $R_4$, $R_6$ and $R_7$ are suitable straight-chain or branched-chain alkyl groups with 1–10 C atoms, such as, for example, methyl, ethyl, propyl, butyl, isobutyl, tert-butyl, pentyl, neopentyl, hexyl, heptyl, decyl. The alkyl groups $R_4$ can optionally be substituted one or more times by halogen atoms, alkoxy groups, optionally substituted aryl or aroyl groups, dialkylamino and trialkylammonium, in which case the simple substitution is to be preferred. As substituents, for example, there can be mentioned fluorine, chlorine or bromine, phenyl, dimethylamino, diethylamino, methoxy, ethoxy. As preferred alkyl groups $R_4$ those with 1–4 C atoms can be mentioned.

If $R_6$ and $R_7$ together with the N atom of radical $R_1=CONR_6R_7$ means an alkylene radical with 3–6 C atoms, the following radicals are meant: azetidine, pyrrolidine, piperidine, azepine.

As aryl groups $R_4$ both substituted and unsubstituted aryl groups are suitable, such as, for example, phenyl, 1-naphthyl and 2-naphthyl which can be respectively substituted by 1–3 halogen atoms (F, Cl, Br), a phenyl group, 1–3 alkyl groups with 1–4 C atoms each, a chloromethyl group, fluoromethyl group, trifluoromethyl group, carboxyl group, hydroxy group or alkoxy group with 1–4 C atoms. Preferred substituents in 3- and 4-position in a phenyl ring are, for example, fluorine, chlorine, alkoxy or trifluoromethyl, but in 4-position hydroxy. The aryl radical in the —$CH_2$—CO aryl radical represents a phenyl or naphthyl radical, which optionally can be substituted by halogen (chlorine, bromine), trifluoromethyl or phenyl.

The cycloalkyl groups $R_4$ can contain in the ring 3–10 carbon atoms preferably 5 and 6 carbon atoms. The rings can be substituted by alkyl groups with 1–4 carbon atoms. For example, there can be mentioned cyclopentylhexyl, cyclohexyl, methylcyclohexyl.

As heterocyclic groups $R_4$, 5- and 6-member heterocycles, which contain at least 1 heteroatom, preferably nitrogen, oxygen or sulfur, are suitable. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, i.a.

As acid radicals $R_5$ physiologically compatible acid radicals are suitable. Preferred acids are organic carboxylic acids and sulfonic acid with 1–10 carbon atoms, which belong to the aliphatic, cycloaliphatic, aromatic, aromatic-aliphatic and heterocyclic series. These acids can be saturated, unsaturated and/or polybasic and/or substituted in the usual way. As examples for the substituents, there can be mentioned alkyl groups, hydroxy groups, alkoxy groups, oxo groups or amino groups or halogen atoms. For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, trimethylacetic acid, diethylacetic acid, tertbutylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted with halogen groups, trifluoromethyl groups, hydroxy groups, alkoxy groups or carboxy groups, nicotinic acid, isonicotinic acid, 2-furancarboxylic acid, cyclopentylpropionic acid. As especially preferred acyl radicals and alkanesulfonyl radicals, those with up to 6 carbon atoms are possible. As sulfonic acids, for example, methanesulfonic acid, ethanesulfonic acid, isopropanesulfonic acid, betachloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis-(beta-chloroethyl)aminosulfonic acid, N,N-diisobutylaminosulfonic acid, N,N-dibutylaminosulfonic acid, pyrrolidino-, piperidino-, piperazino-, N-methylpiperazino-and morpholinosulfonic acid are possible.

As alkyl groups $R_3$ straight- and branched-chain, saturated and unsaturated alkyl radicals, preferably saturated, with 1–10, especially 1–6 C atoms, are suitable, which optionally can be substituted by optionally substituted aryl. For example, there can be mentioned the methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups. If alkyl groups $R_3$ are halogen-substituted the halogens fluorine, chlorine and bromine are suitable.

The cycloalkyl group $R_3$ can contain in the ring 3–10 carbon atoms, preferably 3–6 carbon atoms. The rings can be substituted by alkyl groups with 1–4 carbon atoms. For example, there can be mentioned cyclopropyl, cyclobutyl, cyclopentyl, cyclohexyl, methylcyclohexyl.

As substituted or unsubstituted aryl groups $R_3$ for example, phenyl, 1-naphthyl and 2-naphthyl, which can each be substituted by 1-3 halogen atoms, a phenyl group, 1-3 alkyl groups each with 1–4 C atoms, a chloromethyl group, fluoromethyl group, trifluoromethyl group, carboxyl group, $C_1$–$C_4$ alkoxy group or hydroxy group are suitable. The substitution in 3- and 4-position in a phenyl ring is preferable, for example, by fluorine, chlorine, alkoxy or trifluoromethyl or in 4-position by hydroxy.

As heterocyclic groups $R_3$,5- and 6-member heterocycles that contain at least 1 heteroatom, preferably nitrogen, oxygen or sulfur, are suitable. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a.

As alkylene group B, straight-chain or branched-chain, saturated and unsaturated alkylene radicals with up to 10 C atoms, preferably saturated with 1–10, especially with 1–5 C atoms, which can be substituted optionally by fluorine atoms, are suitable. For example, there can be mentioned: methylene, fluoromethylene, difluoromethylene, ethylene, 1,2-propylene, ethylethylene, trimethylene, tetramethylene, pentamethylene, 1,1-difluoroethylene, 1-fluoroethylene, 1-methyltetramethylene, 1-methyl trimethylene, 1-methylene-ethylene, 1-methylene-tetramethylene.

As acid radicals $R_2$, physiologically compatible acid radicals are suitable. Preferred acids are organic carboxylic acids and sulfonic acids with 1–15 carbon atoms, which belong to the aliphatic, cycloaliphatic, aromatic, aromatic-aliphatic or heterocyclic series. These acids can be saturated, unsaturated and/or polybasic and/or substituted in the usual way. As examples for the substituents, there can be mentioned the alkyl, hydroxy, alkoxy, oxo or amino groups or halogen atoms.

For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and tri-chloroacetic acid, aminoacetic acid, diethylaminoacetic acid, piperidinoacetic acid, morpholinoacetic acid, lactic acid, succinic acid, adipic acid, benzoic acid, benzoic acids substituted with halogen, trifluoromethyl, hydroxy, alkoxy or carboxy groups, nicotinic acid, isonicotinic acid, 2-furancarboxylic acid, cyclopentylpropionic acid. As especially preferred acid radicals $R_2$, acyl radicals with up to 10 carbon atoms are suitable.

Inorganic and organic bases are suitable for salt formation, as they are known to one skilled in the art for forming physiologically compatible salts. For example, there can be mentioned alkali hydroxides, such as sodium and potassium hydroxide, alkaline earth hydroxides, such as calcium hydroxide, ammonia, amines, such as ethanolamine, diethanolamine, triethanolamine, n-methylglucamine, morpholine, tris-(hydroxymethyl)-methylamine, etc.

The leukotriene-$B_4$ derivatives of formula 1 form the already mentioned cyclodextrin clathrates with alpha-, beta-, gamma-cyclodextrin.

The invention further contains a process for the production of leukotriene-$B_4$ derivatives of formula I, which is characterized in that a vinyl halide of formula II or III

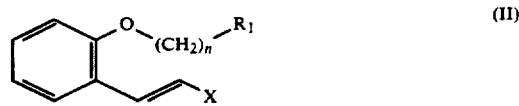

or

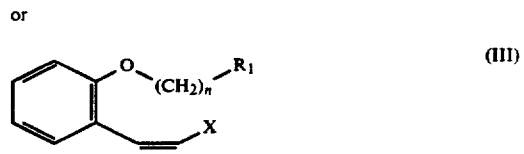

in which $R_1$ and n have the meanings already indicated and X is an iodine or bromine atom, is reacted with a tin organic compound of formula IV

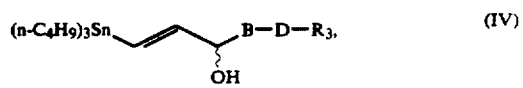

in which B, D and $R_3$ have the meanings already indicated, with the help of a palladium catalyst and optionally separated then in any sequence of enantiomers, protected hydroxy groups are released and/or a free hydroxy group is esterified and/or the 1-hydroxy group is oxidized to carboxylic acid and/or double bonds are hydrogenated and/or an esterified carboxyl group ($R_1 = COOR_4$) is saponified and/or reduced and/or a carboxyl group ($R_4 = H$) is esterified and/or a free carboxyl group ($R_4 = H$) is converted to an amide or a carboxy group with a physiologically compatible base is converted to a salt.

The initial compounds of formula II and III can be produced according to the following methods:

Method A [analogous to K. Takai et al. J. Amer. Chem. Soc. 108 (1986) 7408]:

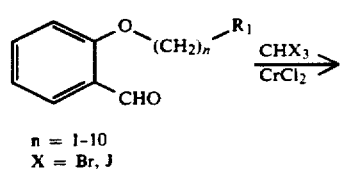

n = 1-10
X = Br, J

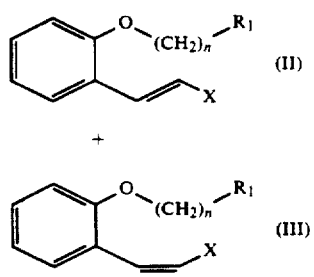

Method B [analogous to R. A. Haack et al. Tetrahedron Letters 29 (1988) 2783]:

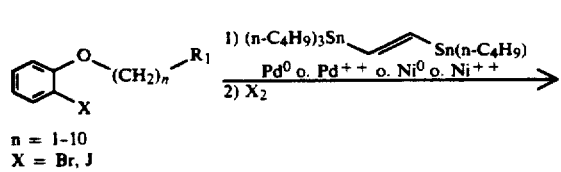

n = 1-10
X = Br, J

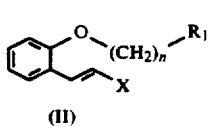

For the reaction according to method B and for the reaction of compounds of formulas II and III with IV, nickel and palladium catalysts are suitable, for example, 1,3-bis-(diphenylphosphino)-propanenickel(II) chloride, tetrakis(triphenylphosphine)-nickel, bis-tri-o-tolyl-phosphine-palladium(II) chloride, bis(triphenylphosphine)-palladium(II) chloride, tetrakis(triphenylphosphine)-palladium, 1,1'-bis(diphenylphosphino)-ferrocene palladium(II) chloride and bis(acetonitrile)-palladium(II) chloride.

The initial compounds of formula IV are produced as follows:

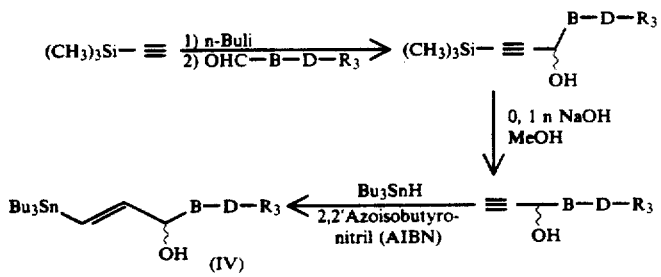

in which B, D and $R_3$ have the above-indicated meanings.

The reaction of

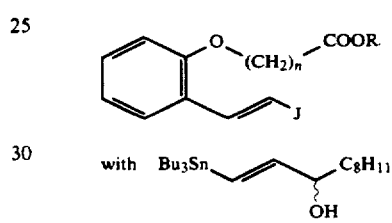

in the presence of Pd to

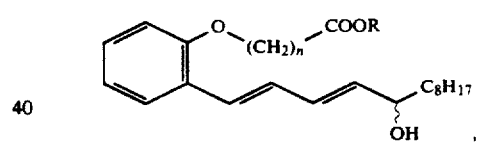

a compound according to formula I, is performed according to J. K. Stille et al. J. Amer. Chem. Soc. 109 (1987) 2143.

The compound

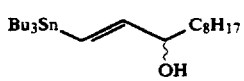

can be reacted to

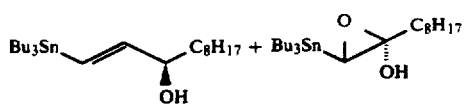

with the Sharpless epoxidation [Y. Gao . . . and K. B. Sharpless J. Amer. Chem. Soc. 109 (1987) 5765].

After chromatographic separation, there is obtained

which with

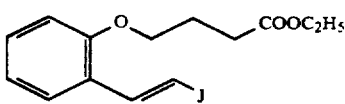

yields the beta-isomer in the presence of Pd.

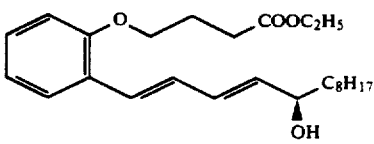

The initial compounds of method A

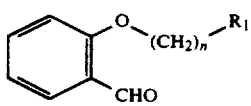

are obtained from salicylaldehyde by reaction with bromoalkanoic acid esters in the presence of NaH.

The initial compounds of method B

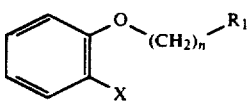

are obtained from o-iodophenol or o-bromophenol and w-bromoalkanoic acid esters (alkane=ethane, butane, pentane) in DMF in the presence of $Cs_2CO_3$ at room temperature in an 80% yield.

All compounds of formula I produced up to the compound of example 3 represent racemates. The racemates can be separated in an "optically active" column (Chiralcel-OD column).

The reduction in the compounds of formula I with $R_1$ meaning a —$CH_2OH$ group is performed with a reducing agent suitable for the reduction of esters or carboxylic acids, such as, for example, lithium aluminum hydride, diisobutyl aluminum hydride, etc. As solvents, diethyl ether, tetrahydrofuran, dimethoxyethane, toluene, etc., are suitable. The reduction is performed at temperatures of $-30°$ C. up to the boiling temperature of the solvent used, preferably $0°$ C. to $30°$ C.

The esterification of the alcohols of the formula I ($R_2$=H) takes place in a way known in the art. For example, the esterification takes place in that an acid derivative, preferably an acid halide or an acid anhydride, is reacted in the presence of a base such as, for example, Na hydride, pyridine, triethylamine, tributylamine or 4-dimethylaminopyridine with an alcohol of formula I. The reaction can be performed without a solvent or in an inert solvent, preferably acetone, acetonitrile, dimethylacetamide, DMSO at temperatures above or below room temperature, for example, between $-80°$ C. to $100°$ C., preferably at room temperature.

The saponification of the esters of formula I is performed according to methods known to one skilled in the art, such as, for example, with basic catalysts. The compounds of formula I can be separated by the usual separating methods into the optical isomers.

The saponification of the acyl groups takes place, for example, with alkali or alkaline-earth carbonates or hydroxides in an alcohol or in the aqueous solution of an alcohol. As an alcohol, aliphatic alcohols are suitable, such as, for example, methanol, ethanol, butanol, etc., preferably methanol. As alkali carbonates and alkali hydroxides, potassium and sodium salts can be mentioned. The potassium salts are preferred.

As alkaline-earth carbonates and hydroxides, for example, calcium carbonate, calcium hydroxide and barium carbonate are suitable. The reaction takes place at $-10°$ C. to $+70°$ C., preferably at $+25°$ C.

The introduction of the ester group

for $R_1$, in which $R_4$ represents an alkyl group with 1-10 C atoms, takes place according to methods known to one skilled in the art. The 1-carboxy compounds are reacted, for example, with diazohydrocarbons in a way known in the art. The esterification with diazohydrocarbons takes place, e.g., in that a solution of the diazohydrocarbon in an inert solvent, preferably in diethyl ether, is mixed with the 1-carboxy compound in the same or in another inert solvent, such as, e.g., methylene chloride. After completion of the reaction in 1 to 30 minutes, the solvent is removed and the ester is purified in the usual way. Diazoalkanes are either known or can be produced according to known methods [Org. Reactions Vol. 8, pages 389–394 (1954)].

The introduction of the ester group

for $R_1$, in which $R_4$ represents a substituted or unsubstituted aryl group, takes place according to methods known to one skilled in the art. For example, the 1-carboxy compounds in an inert solvent with the corresponding arylhydroxy compounds are reacted with dicyclohexylcarbodiimide in the presence of a suitable base, for example pyridine, DMAP, triethylamine. As a solvent, methylene chloride, ethylene chloride, chloroform, ethyl acetate, tetrahydrofuran, preferably chloroform are suitable. The reaction is performed at temperatures between $-30°$ C. and $+50°$ C., preferably at $10°$ C.

If C=C double bonds contained in the primary product are to be reduced, the hydrogenation takes place according to methods known in the art.

The hydrogenation of the $delta^{8,10}$-diene system is performed, in a way known in the art, at low temperatures, preferably at about $-20°$ C. to $+30°$ C. in a hydrogen atmosphere in the presence of a noble metal catalyst. As a catalyst, for example, 10% palladium on carbon is suitable.

The leukotriene-$B_4$ derivatives of formula I with $R_4$ meaning a hydrogen atom can be converted to a salt with suitable amounts of the corresponding inorganic bases with neutralization. For example, during the release of the corresponding acids in water, which contains the stoichiometric amount of the base, the solid inorganic salt is obtained after the evaporating off of the water or after the addition of a water-miscible solvent, e.g., alcohol or acetone.

For the production of an amino salt, the LTB$_4$ acid, e.g., is dissolved in a suitable solvent, for example, ethanol, acetone, diethyl ether, acetonitrile or benzene, and at least the stoichiometric amount of the amine is added to this solution. In this way, the salt usually accumulates in solid form or is isolated after evaporation of the solvent in the usual way.

Another possibility for the introduction of the amide groups

for R$_1$ is in the reaction of a 1-carboxylic acid of formula I (R$_4$=H), in which free hydroxy groups optionally are protected intermediately with compounds of formula V $$O=C=N-R_5 \qquad (V)$$

in which R$_5$ has the above-indicated meaning.

The reaction of the compound of formula I (R$_4$=H) with an isocyanate of formula V optionally takes place by adding a tertiary amine such as, e.g., triethylamine or pyridine. The reaction can be performed without a solvent or in an inert solvent, preferably acetonitrile, tetrahydrofuran, acetone, dimethylacetamide, methylene chloride, diethyl ether, toluene at temperatures between −80° C. to 100° C., preferably at 0° C. to 30° C.

The compounds of formula 1 act in an anti-inflammatory and anti-allergic manner. In addition, they have antimycotic properties. Consequently, the new leukotriene-B$_4$ derivatives of formula 1 represent valuable pharmaceutical active ingredients. The compounds of formula I are especially suitable for topical application, since they exhibit a dissociation between desirable topical effectiveness and undesirable systemic side effects.

The new leukotriene-B$_4$ derivatives of formula 1 are suitable in combination with the auxiliary agents and vehicles usual in galenic pharmaceutics for topical treatment of contact dermatitis, eczemas of the most varied types, neurodermatosis, erythrodermia, burns, tinea, pruritus vulvae, pruritus ani, rosacea, lupus erythematosus cutaneus, psoriasis, lichen ruber planus and verrucosis and similar skin diseases.

The production of pharmaceutical agent specialties takes place in the usual way, by the active materials with suitable additions being converted into the desired form of application, such as, for example: solutions, lotions, ointments, creams or plasters. In the pharmaceutical agents thus formulated, the active ingredient concentration is dependent on the form of application. An active ingredient concentration of 0.0001% to 1% is used preferably in lotions and ointments.

Further, the new compounds optionally in combination with the usual vehicles and auxiliary agents are also very suitable for the production of inhalants, which can be used for the treatment of allergic diseases of the respiratory system such as, for example, bronchial asthma or rhinitis.

Further, the new leukotriene-B$_4$ derivatives also are suitable in the form of capsules, tablets or coated tablets, which preferably contain 0.1 to 100 mg of active ingredient or are applied orally in the form of suspensions, which preferably contain 1-200 mg of active ingredient per dosage unit, and are also applied rectally to treat allergic diseases of the intestinal track, such as colitis ulcerosa and colitis granulomatosa.

The new leukotriene-B$_4$ derivatives can also be used combined with, e.g., lipoxygenase inhibitors, cyclooxygenase inhibitors, prostacyclin agonists, thromboxane antagonists, leukotriene-D$_4$ antagonists, leukotriene-E$_4$ antagonists, leukotriene-F$_4$ antagonists, phosphodiesterase inhibitors or PAF antagonists.

EXAMPLE 1

A. A solution of 12.2 g of salicylaldehyde in 20 ml of dimethylformamide is instilled into a suspension of 4.36 g of sodium hydride (55% dispersion in mineral oil) in 80 ml of dimethylformamide by stirring and ice cooling within 15 minutes. After 3 hours, a solution of 21.5 g of 4-bromobutyric acid ethyl ester in 16 ml of dimethylformamide is instilled by ice cooling within 15 minutes, and the mixture is stirred for 72 hours at room temperature. The batch is poured on ice/water, shaken with ether, the organic phase is washed briefly with 1 n sodium hydroxide solution, dried with sodium sulfate and concentrated by evaporation. The crude product is distilled at 130°-140° C./0.1 mbar in a bulb tube and 11.2 g of 4-(2-formylphenoxy)-butyric acid ethyl ester is thus obtained as a colorless oil.

IR: 2980, 2938, 2871, 1733, 1688, 1599, 1458, 1242, 1043, 760 cm$^{-1}$.

B. A solution of 7.9 g of iodoform and 2.36 g of 4-(2-formylphenoxy)-butyric acid ethyl ester in 50 ml of tetrahydrofuran is instilled in a suspension of 7.4 g of chromium(II) chloride in 100 ml of tetrahydrofuran at 0° C. and argon atmosphere. After 2½ hours, the mixture is diluted with water, shaken with diethyl ether, the organic phase is dried with sodium sulfate, concentrated by evaporation and the oil residue is chromatographed on silica gel with hexane/ethyl acetate 95/5. Thus 1.9 g of a yellow oil is obtained that consists of 50% of 4-[2-[(E)-2-iodovinyl]-phenoxy]-butyric acid ethyl ester (I) 50% of 4-[2-[(Z)-2-iodovinyl]-phenoxy]-butyric acid ethyl ester (II). This E/Z mixture is separated on silanized silica gel (RP-18 material) with high-pressure liquid chromatography.

I: IR: 2978, 1732, 1595, 1451, 1245, 1179, 1102, 1049, 952, 750 cm$^{-1}$;

II: IR: 2978, 1732, 1595, 1485, 1451, 1250, 1178, 1107, 1049, 752 cm$^{-1}$.

C. Analogously to example 1B, 3.7 g of chromium(II) chloride in 50 ml of tetrahydrofuran and a solution of 3.95 g of iodoform and 1.18 g of 4-(2-formylphenoxy)-butyric acid ethyl ester in 20 ml of tetrahydrofuran are added together, mixed with 581 mg of tetramethylthylenediamine, and the mixture is refluxed for 6 hours. After a working up analogously to example 1B and chromatography on silica gel, 660 mg of yellow oil is obtained that consists of 70% from 4-[2-[(E)-2-iodovinyl]-phenoxy]-butyric acid ethyl ester and 30% of 4-[2-(Z-2-iodovinyl)phenoxy]-butyric acid ethyl ester.

D. A solution of 154 mg of 4-[2-[(E)-2-iodovinyl]-phenoxy]-butyric acid ethyl ester in 2 ml of dimethylformamide is mixed with 6 mg of bis-(acetonitrile)-palladium(II) chloride and stirred for 10 minutes at room temperature. Then 217 mg of (E)-1-(tri-n-butylstannyl)-1-undecen-(3RS)-3-ol is added and the mixture is stirred for 4 hours at room temperature. The reaction mixture is concentrated by evaporation and the residue is chromatographed on silica gel with n-hexane/ethyl acetate=85/15. 100 mg of 4-[2-[(1E,3E)-(5RS)-5-hydroxy-1,3-tridecadienyl]-phenoxy]-butyric acid ethyl ester is obtained as a colorless oil.

IR: 3460, 2925, 2857, 1735, 1600, 1490, 1455, 1245, 1180, 1050, 752 cm$^{-1}$.

The organotin compound used in example 1D is produced as follows:

E. (E)-1-(tri-n-butylstannyl)-1-undecen-(3RS)-3-ol a) 173 mol of n-butyllithium solution (1.6 mol in hexane) is instilled in a solution of 25 g of trimethylsilylacetylene in 500 ml of tetrahydrofuran with stirring and argon atmosphere at −40° C., is stirred for 30 minutes at −40° C., cooled to −70° C. and 48.1 ml of nonanal is instilled at this temperature. After an hour at −70° C., the mixture is allowed to come to −30° C., 300 ml of 2 n hydrochloric acid is added and shaken with diethyl ether. The organic phases are dried (Na$_2$SO$_4$), concentrated by evaporation and the residue is distilled in a bulb tube at 120°-130° C./0.2 mbar. Thus 48.5 of (3RS)-1-(trimethylsilyl)-1-undecin-3-ol is obtained as a colorless oil.

IR: 3350, 2965, 2930, 2860, 2178, 1250, 843, 760 cm$^{-1}$.

b) 10 g of (3RS)-1-(trimethylsilyl)-1-undecin-3-ol is dissolved in a mixture of 420 ml of 0.1 n sodium hydroxide solution and 420 ml of methanol and stirred for 3 hours at room temperature. Then, the methanol is removed in a vacuum, shaken with diethyl ether, dried (Na$_2$SO$_4$) and concentrated by evaporation. 6.46 g of (3RS)-1-undecin-3-ol is obtained as a yellow oil, which is further reacted as a crude product.

IR: 3318, 2925, 2855, 1680, 1467, 1460, 1380, 1030, 655, 627 cm$^{-1}$.

c) A mixture of 3 g of (3RS)-1-undecin-3-ol, 7.12 ml of tri-n-butyltin hydride and 36 ml of 2,2'-azoisobutyric acid nitrile is heated under argon atmosphere for 2 hours to 80° C. The reaction mixture is chromatographed with n-hexane on silica gel, which is deactivated with 2% (percent by weight) of triethylamine. 4.4 g of (E)-1-tri-n-butylstannyl)-1-undecen-(3RS)-3-ol is obtained as a colorless oil.

IR: 3340, 2958, 2929, 2858, 1465, 1377, 1072, 990 cm$^{-1}$.

EXAMPLE 2

4-[2-[(1E,2E)-(5RS)-5-hydroxy-1,3-tridecadienyl]-phenoxy]-butyric acid ethyl ester A. 8.65 g of bromophenol and 8.75 g of 4-bromobutyric acid ethyl ester are dissolved in 120 ml of dimethylformamide, mixed with 32.6 g of cesium carbonate and stirred for 2 days at room temperature. The reaction mixture is filtered, the solvent is distilled off in a vacuum and the residue is distilled in a bulb tube at 180° C./0.4 mbar. 11 g of 4-(2-bromophenoxy)butyric acid ethyl ester is obtained as a colorless oil.

IR: 2980, 1730, 1590, 1469, 1278, 1250, 1180, 1053, 1030, 750 cm$^{-1}$.

B. Under the conditions of example 2A, 25 g of 2-iodophenol and 22.16 g of 4-bromobutyric acid ethyl ester are reacted in 100 ml of dimethylformamide in the presence of 74 g of cesium carbonate, worked up, and 24.2 g of 4-(2-iodophenoxy)butyric acid ethyl ester with a boiling point of 200° C./0.02 mbar is obtained as a colorless oil.

IR: 2980, 1730, 1584, 1465, 1275, 1246, 1180, 1050, 1017, 749 cm$^{-1}$.

C. 861 mg of 4-(2-bromophenoxy)-butyric acid ethyl ester and 4.8 g of (E)-1,2-bis-(tri-n-butylstannyl)-ethylene (50%) are dissolved in 11 ml of toluene, mixed with 70 mg of tetrakis-(triphenylphosphine)-palladium and heated with stirring and under argon atmosphere for 1 hour to 120° C. (bath temperature). After cooling to room temperature, the reaction mixture is diluted with 9 ml of diethyl ether and mixed at 0° C. with a solution of 1.53 g of iodine in 7 ml of diethyl ether. The mixture is stirred for 2 hours at 0° C. and allowed to stand overnight in a refrigerator. The batch is concentrated by evaporation and the residue is chromatographed on silica gel with n-hexane/ethyl acetate=95/5. 810 mg of 4-[2-[(E)-2-iodovinyl]-phenoxy]-butyric acid ethyl ester is obtained as an oily crude product, which is further reacted without further purification.

D. 1.34 g of (4-(2-iodophenoxy)-butyric acid ethyl ester and 6.4 g of (E)-1,2-bis-(tri-n-butylstannyl)-ethylene (50%) are dissolved in 12 ml of toluene, mixed with 94 mg of tetrakis-(triphenylphosphine)-palladium and heated with stirring and argon atmosphere for 2 hours to 70°-80° C. (bath temperature). After cooling to room temperature, the reaction mixture is diluted with 12 ml of diethyl ether and treated with a solution of 2.04 g of iodine in 10 ml of diethyl ether, worked up and chromatographed on silica gel with n-hexane/ethyl acetate=95/5 under the conditions of example 2C. 900 mg of 4-[-[(E)-2-iodovinyl]-phenoxy]-butyric acid ethyl ester is obtained as a yellow oil.

IR: see example 1B:I

E. Under the conditions of example 1D, 400 mg of 4-[-[(E)-2-iodovinyl]-phenoxy]-butyric acid ethyl ester in 2 ml of dimethylformamide, obtained according to example 2C or 2D, in the presence of 36 mg of 1,1'-bis-(diphenylphosphino)-ferrocene pallium(II) chloride is reacted with 460 mg of (E)-1-(tri-n-butylstannyl)-1-undecen-(3RS)-3-o1, worked up and chromatographed on silica gel with n-hexane/ethyl acetate=9/1. 160 mg of 4-[2-[(1E,3E)-(5RS)-5-hydroxy-1,3-tridecadienyl]-phenoxy]-butyric acid ethyl ester is obtained as a colorless oil.

IR: See example 1D.

EXAMPLE 3

4-[2-[(1E,3E)-(5R)-5-hydroxy-1,3-tridecadienyl]-phenoxy]-butyric acid ethyl ester A. A mixture of 917 mg of (E)-1-(tri-n-butylstannyl)-1-undecen-(3RS)-3-o1, 112.6 mg of L-(+)-tartaric acid diisopropylester and 275 mg of a pulverized molecular sieve (3 angstroms) in 4 ml of methylene chloride is mixed at −15° C. with 113.7 mg of titanium(IV) isopropylate and stirred for 20 minutes at −20° C. Then, 1 ml of tert-butyl hydroperoxide (3 molar in isooctane) is added at −20° C. and the mixture is stirred for 4 hours at this temperature. The batch is mixed at 0° C. with a solution of 3.3 g of iron(II) sulfate and 1 g of tartaric acid in 10 ml of water and stirred for 10 minutes at 0° C. Then, it is shaken out with diethyl ether, the organic phase is dried (Na$_2$SO$_4$), concentrated by evaporation and the crude product is chromatographed on silica gel with n-pentane/diethyl ether=95/5. 245 mg of (E)-1-(tri-n-butylstannyl)-1-undecen-(3R)-3-ol is obtained as a colorless oil.

[α]$_D$= −9.3° (2% in ethanol).
IR: see Example 1E, c.

B. Under the conditions of example 1D, 115 mg of 4-[2-[(E)-2-iodovinyl)phenoxy]-butyric acid ethyl ester in 2 ml of dimethylformamide in the presence of 11.5 g of 1,1'-bis-(diphenylphosphino)-ferrocene palladium(II) chloride is reacted with 147 mg of (E)-1-(tri-n-butylstannyl)-1-undecen-(3R)-3-ol, worked up and chromatographed on silica gel with n-hexane/ethyl acetate=9/1. 55 mg of 4-[2-[(1E,3E)-(5R)-5-hydroxy-1,3-tridecadienyl]-phenoxy]-butyric acid ethyl ester is obtained as a colorless oil.

[α]$_D$= −12° (5% in ethanol).
IR: see example 1D.

C. 10 mg of 4-[2-[(1E,3E)-(5R)-5-hydroxy-1,3-tridecadienyl]-phenoxy]-butyric acid ethyl ester is obtained by racemate separation of 50 mg of 4-[2-[(1E,3E)-(5RS)-5-hydroxy-1,3-tridecadienyl]-phenoxy]-butyric acid ethyl ester on a Chiralcel-OD column with high-pressure liquid chromatography and n-hexane/isopropanol=8/2 as an eluant.

[α]$_D$= −12.6° (5% in ethanol)

EXAMPLE 4

4-[2-[(1Z,3E)-(5RS)-5-hydroxy-1,3-tridecadienyl]-phenoxy]-butyric acid ethyl ester Under the conditions of example 1D, 180 mg of 4-[2-[(Z)-2-iodovinyl]-phenoxy]-butyric acid ethyl ester in 2 ml of dimethylformamide in the presence of 7 mg of bis-(acetonitrile)palladium(II) chloride is reacted with 254 mg of (E)-1-(tri-n-butylstannyl)-1-undecen-(3RS)-3-ol, worked up and chromatographed on silica gel with n-hexane/ethyl acetate-98/2. 95 mg of 4-[2-[(1Z,3E)-(5RS)-5-hydroxy-1,3-tridecadienyl]-phenoxy]-butyric acid ethyl ester is obtained as a colorless oil.

IR: 3460, 2922, 2850, 1735, 1597, 1488, 1401, 1245, 1178, 1050, 750 cm$^{-1}$.

EXAMPLE 5

4-[2-[(1E,3E)-(5RS)-5-hydroxy-1,3-tridecadienyl]-phenoxy]-butyric acid methyl ester A. A solution of 2 g of 4-(2-bromophenoxy)-butyric acid ethyl ester in 20 ml of methanol and 20 ml in sodium hydroxide solution is stirred for 2 hours at room temperature, then acidified with 0.1 n hydrochloric acid and extracted with diethyl ether. The organic phase is dried (Na$_2$SO$_4$), concentrated by evaporation and 1.4 g of 4-(2-bromophenoxy)-butyric acid with a melting point 80°-81° C. is obtained.

IR: 3518, 3060, 2960, 1710, 1588, 1467, 1442, 1275, 1245, 1125, 1050, 1030, 952 cm$^{-1}$.

B. A solution of 1.4 g of 4-(2-bromophenoxy)-butyric acid in 22 ml of methanol is mixed with 1 g of Amberlyst 15 and stirred for 5 hours at room temperature. Then, it is filtered from the Amberlyst 15, the filtrate concentrated by evaporation, the residue is taken up in diethyl ether, washed with dilute sodium carbonate solution, dried (Na$_2$SO$_4$) and concentrated by evaporation. 1.5 g of 4-(2-bromophenoxy)-butyric acid methyl ester is obtained as a colorless oil.

IR: 2970, 1735, 1590, 1483, 1470, 1442, 1278, 1249, 1175, 1053, 1030, 750 cm$^{-1}$.

C. Under the conditions of example 2C, 482 mg of 4-(2-bromophenoxy)-butyric acid methyl ester and 3.2 g of (E)-1,2-bis-(tri-n-butylstannyl)-ethylene (50%) in 6 ml of toluene are heated in the presence of 47 mg of tetrakis-(triphenylphosphine)-palladium, diluted with 6 ml of diethyl ether, mixed with a solution of 1.02 g of iodine in 5 ml of diethyl ether, concentrated by evaporation, and the residue is chromatographed on silica gel. 400 mg of 4-[2-[(E)-2-iodovinyl]-phenoxy]butyric acid methyl ester is obtained as an oily crude product, which is used in the next stage without further purification.

D. Under the conditions of example 1D, 400 mg of 4-[-2-[(E)-2-iodovinyl]-phenoxy]butyric acid methyl ester in the presence of 16.2 mg of bis-(acetonitrile)-palladium(II) chloride is reacted with 599 mg of (E)-1-(tri-n-butylstannyl)-1-undecen-(3RS)-3-ol, worked up and chromatographed. 125 mg of 4-[2-[(1E,3E)-(5RS)-5-hydroxy-1,3-tridecadienyl]-phenoxy]butyric acid methyl ester is obtained as a colorless oil, which is subjected for complete purification to high-pressure liquid chromatography on silanized silica gel (RP 18-material) with methanol/water=8/2.

IR: 3430, 2925, 2855, 1738, 1595, 1490, 1455, 1242, 1171, 1050, 971, 749 cm$^{-1}$.

EXAMPLE 6

4-[2-[(1E,3E)-(5RS)-5-hydroxy-1,3-tridecadienyl]-phenoxy]-butyric acid isopropylester A. Under the conditions of example 5A, 1 g of 4-(2-iodophenoxy)-butyric acid ethyl ester in 10 ml of methanol and 10 ml of 1 n sodium hydroxide solution is saponified, worked up, and 900 mg of 4-(2-iodophenoxy)-butyric acid methyl ester with a melting point of 66.5°-67° C. is obtained.

IR: 3510, 2940, 2670, 1710, 1585, 1467, 1440, 1278, 1050, 1018, 953, 648 cm$^{-1}$.

B. A solution of 4-(2-iodophenoxy)-butyric acid in 10 ml of isopropanol is mixed with 0.5 g of Amberlyst 15, stirred overnight at room temperature and then refluxed for 2 hours. Then, it is filtered from the Amberlyst 15, the filtrate is concentrated by evaporation, the residue is taken up in diethyl ether, washed with diluted sodium carbonate solution, dried and concentrated by evaporation. 920 mg of 4-(2-iodophenoxy)butyric acid isopropylester is obtained as a colorless oil.

IR: 2962, 2938, 1718, 1584, 1465, 1438, 1325, 1275, 1260, 1245, 1102, 1015, 943, 646 cm$^{-1}$.

C. Under the conditions of example 2D, 696 mg of 4-(2-iodophenoxy)-butyric acid isopropylester and 3.2 g of (E)-1,2-bis-(tri-n-butylstannyl)-ethylene (50%) are reacted in the presence of 47 mg of tetrakis (triphenylphosphine)palladium, treated with 1.02 g of iodine, worked up and chromatographed on silica gel with n-hexane/ethyl acetate 9/1. 340 mg of 4-[2-[(E)-2-iodovinyl]-phenoxy]butyric acid propylester is obtained as an oily crude product, which is used without further purification in the next stage.

D. Under the conditions of example 1D, 330 mg of 4-[-2-[(E)-2-iodovinyl]-phenoxy]butyric acid isopropylester in the presence of 32 mg of 1,1'-bis-(diphenylphosphino)-ferrocene palladium(II) chloride is reacted with 445 mg of (E)-1-(tri-n-butylstannyl)-1-undecen-(3RS)-3-ol, worked up and chromatographed on silica gel with n-hexane/ethyl acetate=95/5. 189 mg of 4-[2-[(1E,3E)-(5RS)-5-hydroxy-1,3-tridecadienyl]-phenoxy]-butyric acid isopropylester is obtained as a colorless oil, which is subjected for complete purification to high-pressure liquid chromatography on silanized silica gel (RP 18 material) with methanol/water=8/2.

IR: 2928, 2860, 1722, 1600, 1455, 1378, 1260, 1104 cm$^{-1}$.

EXAMPLE 7

4-[2-[(1E,3E)-(5RS)-5-acetoxy-1,3-tridecadienyl]-phenoxy]-butyric acid ethyl ester A solution of 60 mg of 4-[2-[(1E,3E)-(5RS)-5-hydroxy-1,3-tridecadienyl]-phenoxy]-butyric acid ethyl ester in 0.5 ml of pyridine is mixed with ice cooling and under argon atmosphere with 0.12 ml of acetic anhydride and stirred for 4 hours at room temperature. The reaction mixture is concentrated by evaporation and the residue is chromatographed on silica gel with n-hexane/ethyl acetate=95/5. 42 mg of 4-[2-[(1E,3E)-(5RS)-5-acetoxy-1,3-tridecadienyl]-phenoxy]-butyric acid ethyl ester is obtained as a colorless oil.

IR: 3928, 2858, 1735, 1596, 1490, 1455, 1372, 1242, 992, 750 cm$^{-1}$.

EXAMPLE 8

4-[(5RS)-5-hydroxy-tridecyl]-phenoxy]butyric acid ethyl ester

A. Under the conditions of example 1D, 850 mg of 4-[2-[(E/Z)-2-iodovinyl]-phenoxy]butyric acid ethyl ester in the presence of 85 mg of 1,1'-bis-(diphenylphosphino)-ferrocene palladium(II) chloride is reacted with 1.3 g of (1E)-1-(tri-n-butylstannyl)-1-undecen-(3RS)-3-ol, worked up and chromatographed on silica gel with n-hexane/ethyl acetate=9/1. 800 mg of 4-[2-[(1E/Z,3E)-(5RS)-5-hydroxy-1,3-tridecadienyl]-phenoxy]-butyric acid ethyl ester is obtained as a colorless oil.

B. A solution of 400 mg of 4-[2-[(1E/Z,3E)-(5RS)-5-hydroxy-1,3-tridecadienyl]-phenoxy]butyric acid ethyl ester is hydrogenated in the presence of 40 mg of 10% palladium catalyst on activated carbon with shaking for 15 minutes at room temperature and standard pressure. The reaction solution is filtered, concentrated by evaporation and chromatographed on silica gel with n-hexane/ethyl acetate=9/1. 290 mg of 4-[2-[(5RS)-5-hydroxy-tridecyl]-phenoxy]butyric acid ethyl ester is obtained as a colorless oil, which is subjected for complete purification to high-pressure liquid chromatography on silanized silica gel (RP 18 material) with methanol/water=8/2.

IR: 3440, 2928, 2860, 1725, 1600, 1595, 1455, 1375, 1260, 1095 cm$^{-1}$.

EXAMPLE 9

4-[2-[(1E,3E)-(5RS)-5-hydroxy-1,3-tridecadienyl]-phenoxy]-butyric acid

A solution of 130 mg of 4-[2-[(1E,3E)-(5RS)-5-hydroxy-1,3-tridecadienyl]-phenoxy]butyric acid ethyl ester in 10 ml of methanol and 2.5 ml of 0.5 n sodium hydroxide solution is stirred under argon atmosphere for 3 hours at room temperature. The reaction mixture is poured on ice water, acidified to pH 5 with 0.5 n sulfuric acid and shaken out with ethyl acetate. The organic phase is dried, concentrated by evaporation and the residue is chromatographed on silica gel with n-hexane/diethyl ether=7/3. 78 mg of the title compound is obtained as a colorless oil.

IR: 3437, 2920, 2851, 1709, 1594, 1488, 1453, 1240, 1100, 1048, 990, 802, 746 cm$^{-1}$.

EXAMPLE 10

4-[2-[(1Z,3E)-(5RS)-5-hydroxy-1,3-tridecadienyl]-phenoxy]-butyric acid

Under the conditions of example 9, a solution of 60 mg of 4-[2-[(1Z,3E)-(5RS)-5-hydroxy-1,3-tridecadienyl]-phenoxy]-butyric acid ethyl ester in 5 ml of methanol and 2 ml of 0.5 n sodium hydroxide solution is saponified, worked up and chromatographed on silica gel with n-hexane/ethyl acetate=98/2. 55 mg of the title compound is obtained as a colorless oil.

IR: 3436, 2928, 2855, 1712, 1594, 1488, 1450, 1244, 751 cm$^{-1}$.

EXAMPLE 11

4-[2-[(1E,3E)-(5RS)-5-hydroxy-1,3-tridecadienyl]-phenoxy]-butan-1-ol

A. A solution of 250 mg of 4-[2-[(E)-2-iodovinyl]-phenoxy]butyric acid ethyl ester in 5 ml of tetrahydrofuran is instilled into a suspension of 80 mg of lithium aluminum hydride at 0° C. with stirring and under argon atmosphere. Then, it is stirred for an hour with ice cooling, the mixture is decomposed under argon atmosphere with ice water, shaken out with diethyl ether, dried (Na$_2$SO$_4$) and concentrated by evaporation. 120 mg of 4-[2-[(E)-2-iodovinyl]-phenoxy]-butan-1-ol is obtained as a yellow oil, which is further reacted as a crude product.

B. Under the conditions of example 1D, 110 mg of 4-[2-[(E)-2-iodovinyl]-phenoxy]-butan-1-ol in the presence of 13 mg of 1,1'-bis-(diphenylphosphino)-ferrocene palladium(II) chloride is reacted with 200 mg of (E)-1-(tri-n-butylstannyl)-1-undecen-(3RS)-3-ol, worked up and chromatographed on silica gel with n-hexane/ethyl acetate=8/2. 110 mg of 4-[2-[(1E,3E)-(5RS)-5-hydroxy-1,3-tridecadienyl]-phenoxy]-butan-1-ol is obtained as a colorless oil.

IR: 3355, 2925, 2855, 1594, 1487, 1453, 1242, 1100, 1048, 995, 748 cm$^{-1}$.

EXAMPLE 12

2-[2-[(1E,3E)-(5RS)-5-hydroxy-1,3-tridecadienyl]-phenoxy]-ethyl acetate

A. Under the conditions of example 2A, 3 g of 2-iodophenol is reacted in the presence of 8.9 g of cesium carbonate with 2.27 g of bromoethyl acetate, worked up and 1.7 g of 2-(2-iodophenxoy)-ethyl acetate is obtained as a colorless oil of boiling point 170° C./0.4 mbar.

IR: 3065, 2980, 2935, 1740, 1583, 1470, 1445, 1377, 1290, 1200, 1122, 1075, 930, 855, 792, 750, 645 cm$^{-1}$.

B. Under the conditions of example 2D, 612 mg of 2-(2-iodophenoxy)-ethyl acetate and 3.2 g of (E)-1,2-bis-(tri-n-butylstannyl)-ethylene (50%) is reacted in the presence of 47 mg of tetrakis-(triphenylphosphine)-palladium, treated with 1.02 g of iodine, worked up and chromatographed on silica gel with n-hexane/ethyl acetate=95/5. 280 mg of 2-[2-[(E)-2-iodovinyl]-phenoxy]-ethyl acetate is obtained as an oily crude product, which is used without further purification in the next stage.

C. Under the conditions of example 1D, 270 mg of 2-[2-[(E)-2-iodovinyl]-phenoxy]-ethyl acetate in the presence of 29 mg of 1,1'-bis-(diphenylphosphino)-ferrocene palladium (II) chloride is reacted with 410 mg of (E)-1-(tri-n-butylstannyl)-1-undecen-(3RS)-3-ol, worked up and chromatographed on silica gel with n-hexane/ethyl acetate. 200 mg of 2-[2-[(1E,3E)-(5RS)-5-hydroxy-1,3-tridecadienyl]-phenoxy]-ethyl acetate is obtained as a colorless oil, which is subjected for the complete purification to high-pressure liquid chromatography on silanized silica gel (RP 18 material) with methanol/water 85/15.

IR: 2960, 2928, 2855, 1755, 1600, 1485, 1260, 1095, 1010 cm$^{-1}$.

EXAMPLE 13

2-[2-[(1E,3E)-(5RS)-5-hydroxy-1,3-tridecadienyl]-phenoxy]-acetic acid

Under the conditions of example 9, 130 mg of 2-[2-[(1E,3E)-(5RS)-5-hydroxy-1,3-tridecadienyl]-phenoxy]-ethyl acetate is saponified, worked up and the crude product is purified with high-pressure liquid chromatography on silanized silica gel (RP 18 material) with methanol/water/acetic acid=8/2/2%$_1$. 25 mg of the title compound is obtained as a colorless oil.

IR: 3690, 2960, 2928, 2855, 1704, 1260, 1098, 1013 cm$^{-1}$.

EXAMPLE 14

5-[2-[(1E,3E)-(5RS)-5-hydroxy-1,3-tridecadienyl]-phenoxy]-valeric acid ethyl ester A. Under the conditions of example 2A, 3 g of 2-iodophenol in the presence of 8.9 g of cesium carbonate is reacted with 2.84 g of 5-bromovaleric acid ethyl ester, worked up, and 1.8 g of 5-(2-iodophenoxy)valeric acid ethyl ester with a boiling point of 210° C./0.4 mbar is obtained as a colorless oil.

IR: 3060, 2980, 2940, 2870, 1730, 1584, 1467, 1438, 1278, 1248, 1162, 1050, 1018, 750, 650 cm$^{-1}$.

B. Under the conditions of example 2D, 696 mg of 5-(2-iodophenoxy)-valeric acid ethyl ester and 3.2 g of (E)-1,2-bis-(tri-n-butylstannyl)-ethylene (50%) are reacted in the presence of 47 mg of tetrakis-(triphenylphosphine)palladium, treated with 1.02 g of iodine, worked up and chromatographed on silica gel with n-hexane/ethyl acetate-95/5. 430 mg of 5-[2-[(E)-2-iodovinyl]-phenoxy]-valeric acid ethyl ester is obtained as an oily crude product, which is used without further purification in the next stage.

C. Under the conditions of example 1D, 400 mg of 5-[2-[(E)-2-iodovinyl]-phenoxy]-valeric acid ethyl ester in the presence of 39 mg of 1,1'-bis-(diphenylphosphino)-ferrocene palladium(II) chloride is reacted with 540 mg of (E)-1-(tri-n-butylstannyl)-1-undecen-(3RS)-3-ol, worked up and chromatographed on silica gel with n-hexane/ethyl acetate=98/2. 257 mg of 5-[2-[(1E,3E)-(5RS)-5-hydroxy-1,3-tridecadienyl]-phenoxy]-valeric acid ethyl ester is obtained as a colorless oil.

IR: 3500, 2925, 2858, 1723, 1600, 1453, 1375, 1240, 1162, 1100, 992 cm$^{-1}$.

EXAMPLE 15

4-[2-[(1E,3E)-(5RS)-5-hydroxy-1,3-tridecadienyl]-phenoxy]-butyric acid tetramethylenamide A. A solution of 2 g of 4-(2-iodophenoxy)-butyric acid ethyl ester and 200 mg of ammonium chloride in 6 ml of pyrrolidine is refluxed for 2 hours with stirring. The batch is poured into water, shaken out with diethyl ether, the organic phase is washed with 2 n hydrochloric acid and water, dried and concentrated by evaporation. The residue is distilled on a bulb tube at 210° C./0.4 mbar, and 1.6 g of 4-(2-iodophenoxy)-butyric acid tetramethylenamide is obtained as a colorless oil.

IR: 2970, 2875, 1637, 1583, 1462, 1440, 1276, 1247, 1048, 1015, 748 cm$^{-1}$.

B. Under the conditions of example 2D, 718 mg of 4-(2-iodophenoxy)-butyric acid tetramethylenamide and 3.2 g of (E)-1,2-bis-(tri-n-butylstannyl)-ethylene (50%) are reacted in the presence of 47 mg of tetrakis-(triphenylphosphine)palladium, treated with 1.02 g of iodine, worked up and chromatographed on silica gel with n-hexane/ethyl acetate=8/2. 450 mg of 4-[2-[(E)-2-iodovinyl]-phenoxy]-butyric acid tetramethylenamide is obtained as an oily crude product, which is used without further purification in the next stage.

C. Under the conditions of example 1D, 440 mg of 4-[2-[(E)-2-iodovinyl]-phenoxy]-butyric acid tetramethylenamide in the presence of 42 mg of 1,1'-bis-(diphenylphosphino)-ferrocene palladium(II) chloride is reacted with 670 mg of (E)-1-(tri-n-butylstannyl)-1-undecen-(3RS)-3-ol, worked up and chromatographed on silica gel with n-hexane/ethyl acetate=7/3. 150 mg of 4-[2-[(1E,3E)-(5RS)-5-hydroxy-1,3-tridecadienyl]-phenoxy]-butyric acid tetramethylenamide is obtained as a colorless oil.

IR: 2928, 2857, 1625, 1450, 1100, 953 cm$^{-1}$.

We claim:

1. Leukotriene-B$_4$ derivative of formula I, $$\text{(I)}$$

in which n=1-10,

R$_1$ means radical COOR$_4$ with R$_4$ meaning a hydrogen atom, an alkyl radical with 1-10 C atoms, a cycloalkyl radical with 3-10 C atoms, an aryl radical with 6-10 C atoms optionally substituted by 1-2 chlorine, bromine, phenyl, alkyl with 1-4 C atoms, chloromethyl, fluoromethyl, trifluoromethyl, carboxy, C$_1$-C$_4$ alkoxy or hydroxy, a —CH$_2$—CO—aryl radical with 6-10 C atoms for an aryl or a 5-6-member heterocyclic radical with at least 1 heteroatom, A means a cis, trans or trans, trans—CH=CH—CH=CH group or tetramethylene group, B means a straight-chain or branched-chain, saturated or unsaturated alkylene group with up to 10 C atoms which can optionally be substituted by fluorine, or the group with n=1, 2 or 3, D means a direct compound, oxygen, sulfur, a —C≡C group or a —CH=CR$_8$ group with R$_8$ as hydrogen, C$_1$-C$_5$ alkyl, chlorine or bromine, B and D together mean a direct bond, R$_2$ means a hydrogen atom or an acid radical of an organic acid with 1-15 C atoms and R$_3$ means a hydrogen atom, an alkyl radical with 1-10 C atoms, an alkyl radical with 1-10 C atoms substituted by chlorine or bromine, a cycloalkyl radical with 3-10 C atoms; an aryl radical with 6-10 C atoms substituted optionally by 1-2 chlorine, bromine, phenyl, alkyl with 1-4 C atoms, chloromethyl, fluoromethyl, trifluoromethyl, carboxy, C$_1$-C$_4$ alkoxy or hydroxy; or a 5-6-member heterocyclic radical with at least 1 heteroatom and if R$_5$ means a hydrogen atom, their salts with physiologically compatible bases and their cyclodextrin clathrates.

2. Process for the production of leukotriene-B4 derivatives of formula I, according to claim 1, which is characterized in that a vinyl halide of formula II or III

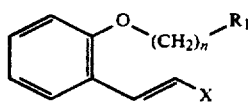 (II)

or

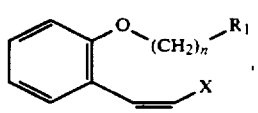 (III)

in which R1 and n have the meanings already indicated and X is an iodine or bromine atom, is reacted with a tin organic compound of formula IV

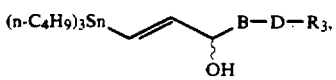 (IV)

in which B, D and R3 have the meanings already indicated, with a palladium catalyst and is optionally then: separated into any sequence of enantiomers or protected hydroxy groups are released or a free hydroxy group is esterified or the 1-hydroxy group is oxidized to carboxylic acid or double bonds are hydrogenated or an esterified carboxyl group (R1=COOR4) is saponified or reduced or a free carboxyl group (R4=H) is esterified or a free carboxyl group (R4=H) is converted to an amide or a carboxy group with a physiologically compatible base is converted to a salt or any combination thereof.

3. Leukotriene-B4 derivative of formula I

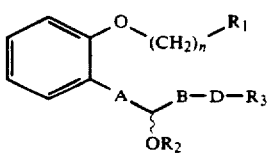 (I)

in which
n=1-10,
R1 means radical COOR4 with R4 meaning a hydrogen atom, an alkyl radical with 1-10 C atoms, a cycloalkyl radical with 3-10 C atoms, an aryl radical with 6-10 C atoms optionally substituted by 1-2 chlorine, bromine, phenyl, alkyl with 1-4 C atoms, chloromethyl, fluoromethyl, trifluoromethyl, carboxy, $C_1$-$C_4$-alkoxy or hydroxy, a —CH2—CO—aryl radical with 6-10 C atoms for an aryl or a 5-6 member heterocyclic radical with at least 1 heteroatom,
A means a cis-, trans-, or trans,trans—CH=CH—CH=CH group,
D means a direct bond,
B and D together mean a direct bond,
R2 means a hydrogen atom, and
R3 means a hydrogen atom, an alkyl radical with 1-10 C atoms, an alkyl radical with 1-10 C atoms substituted by chlorine or bromine, a cycloalkyl radical with 3-10 C atoms; an aryl radical with 6-10 C atoms, or a 5-6 member heterocyclic radical with at least 1 heteroatom and if R4 means a hydrogen atom, their salts with physiologically compatible bases and their cyclodextrin clathrates.

4. A compound selected from the group consisting of:
4-[2-[(1E,3E)-(5RS)-hydroxy-1,3-tridecadienyl]-phenoxy]-butyric acid ethyl ester,
4-[2-[(1E,3E)-(5R)-5-hydroxy-1,3-tridecadienyl]-phenoxy]-butyric acid ethyl ester,
4-[2-[(1Z,3E)-(5RS)-5-hydroxy-1,3-tridecadienyl]-phenoxy]-butyric acid ethyl ester,
4-[2-[(1E,3E)-(5RS)-5-hydroxy-1,3-tridecadienyl]-phenoxy]-butyric acid methyl ester,
4-[2-[(1E,3E)-(5RS)-5-hydroxy-1,3-tridecadienyl]-phenoxy]-butyric acid isopropylester,
4-[2-[(1E,3E)-(5RS)-acetoxy-1,3-tridecadienyl]-phenoxy]-butyric acid ethyl ester,
4-[(5RS)-5-hydroxy-tridecyl]-phenoxy]-butyric acid ethyl ester,
4-[2-[(1E,3E)-(5RS)-5-hydroxy-1,3-tridecadienyl]-phenoxy-butyric acid,
4-[2-[(1Z,3E)-(5RS)-5-hydroxy-1,3-tridecadienyl]-phenoxy-butyric acid,
2-[2-[(1E,3E)-(5RS)-5-hydroxy-1,3-tridecadienyl]-phenoxy]-acetic acid,
5-[2-[(1E,3E)-(5RS)-5-hydroxy-1,3-tridecadienyl]-phenoxy]-butyric acid tetramethylenamide and combinations thereof.

5. Process for the production of leukotriene-B4 derivatives of formula I, according to claim 3, which is characterized in that a vinyl halide of formula II or III

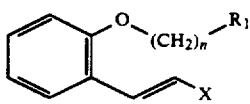 (II)

or

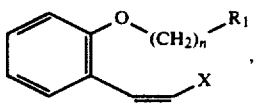 (III)

in which R1 and n have the meanings already indicated and X is an iodine or bromine atom, is reached with a tin organic compound of formula IV

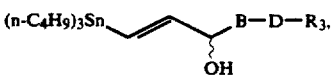 (IV)

in which B, D and R3 have the meanings already indicated, with a palladium catalyst and is optionally then: separated into any sequence of enantiomers or protected hydroxy groups are released or a free hydroxy group is esterified or the 1-hydroxy group is oxidized to carboxylic acid or double bonds are hydrogenated or an esterified carboxyl group (R1=COOR4) is saponified or reduced or a free carboxyl group (R4=H) is esterified or a free carboxyl group (R4=H) is converted to an amide or a carboxy group with a physiologically compatible base is converted to a salt or any combination thereof.

* * * * *